United States Patent [19]

Mennen

[11] 4,340,670
[45] Jul. 20, 1982

[54] METHOD OF USING OVER THE COUNTER SWAB KIT FOR SELF DETECTION OF GONORRHEA IN THE MALE USING TETRAMETHYL CHROMOGEN AMPUL

[76] Inventor: Frederick C. Mennen, 506 Clay St., LaPorte, Ind. 46350

[21] Appl. No.: 275,171

[22] Filed: Jun. 19, 1981

[51] Int. Cl.$^3$ .................... G01N 33/50; C12K 1/00
[52] U.S. Cl. .................... 435/25; 23/230 B; 422/61; 435/37; 435/295; 435/810; 435/871
[58] Field of Search ........... 422/61, 102; 23/230 B; 435/292, 295, 296, 871, 810, 25, 37

[56] References Cited

U.S. PATENT DOCUMENTS

| | | | |
|---|---|---|---|
| 3,446,596 | 5/1969 | Salivar et al. | 422/58 X |
| 3,954,563 | 5/1976 | Mennen | 435/295 |
| 3,954,564 | 5/1976 | Mennen | 435/295 |
| 4,272,479 | 6/1981 | Huneke et al. | 422/61 X |
| 4,300,910 | 11/1981 | Pannwitz | 422/61 X |

*Primary Examiner*—Ronald E. Serwin
*Attorney, Agent, or Firm*—Abraham A. Saffitz

[57] ABSTRACT

An over the counter swab kit for self detection of gonorrhea in the male using an ampul containing 1% N, N, N' N' tetramethyl-p- phenylenediamene or tetramethyl chromogen. The method of taking a sample is also shown in which the open end of a tube is filled with a plug in the form of fibrous material. After a sample is taken of exudate from a male, the 1% solution of tetramethyl chromogen reacts with Neisseria gonorrhea which may be present in the exudate to produce a color change. The plug, before the test, is in a dry condition, the plug is activated only by the tetramethyl chromogen which is placed below the plug in the tube and the ampul broken to release its contents. A sufficient amount of 1% tetramethyl chromogen is held within the frangible ampul to wet the plug and this amount is ½ the volume than is used in the saline ampul in my companion patent application entitled Over the Counter Swab Kit for Self Detection of Gonorrhea in the Male Using Saline Ampul. This volume is drawn by capillary action through the tip on which the sample of exudate was placed and before the ampul was broken. A purple color is created on the tip in 3 minutes at the site of the bacteria and is a positive test for gonorrhea. A key feature of the kit is the cover which protects the tip before use in self diagnosis is removed to take the specimen of exudate, and is replaced when the kit is inverted and the ampul broken to get the color change to purple in 3 minutes. If the deep purple color does not develop this is a negative test.

1 Claim, 5 Drawing Figures

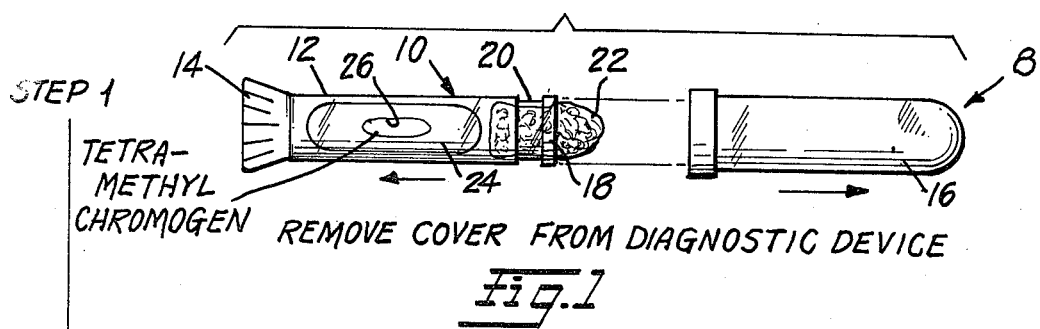

Fig. 1 STEP 1 — TETRA-METHYL CHROMOGEN — REMOVE COVER FROM DIAGNOSTIC DEVICE

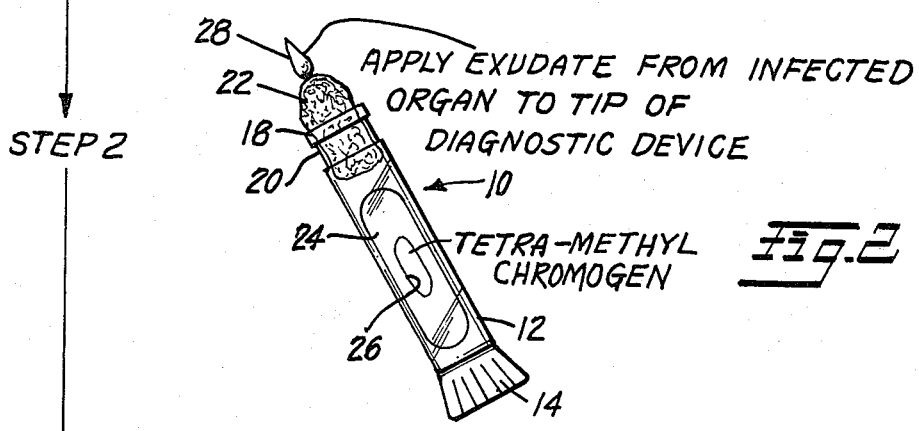

Fig. 2 STEP 2 — APPLY EXUDATE FROM INFECTED ORGAN TO TIP OF DIAGNOSTIC DEVICE — TETRA-METHYL CHROMOGEN

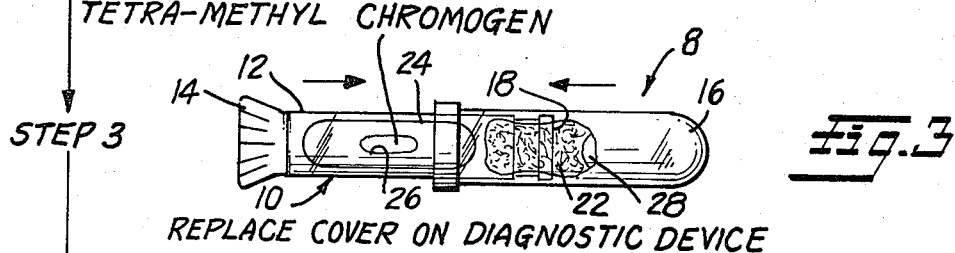

Fig. 3 STEP 3 — TETRA-METHYL CHROMOGEN — REPLACE COVER ON DIAGNOSTIC DEVICE

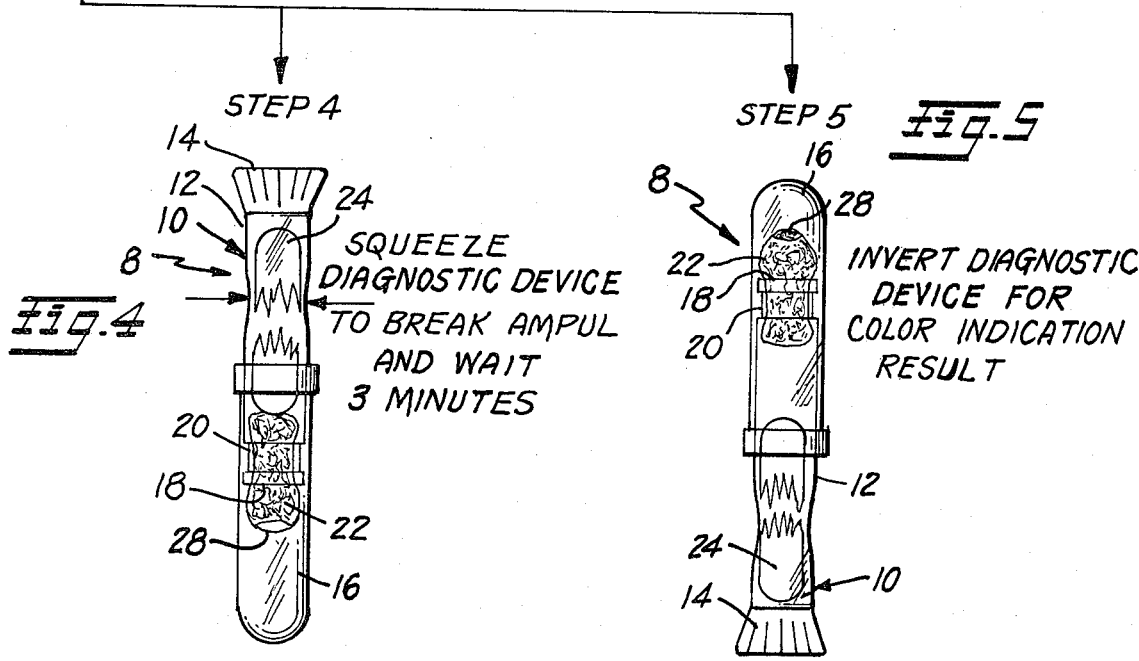

Fig. 4 STEP 4 — SQUEEZE DIAGNOSTIC DEVICE TO BREAK AMPUL AND WAIT 3 MINUTES

Fig. 5 STEP 5 — INVERT DIAGNOSTIC DEVICE FOR COLOR INDICATION RESULT

METHOD OF USING OVER THE COUNTER SWAB KIT FOR SELF DETECTION OF GONORRHEA IN THE MALE USING TETRAMETHYL CHROMOGEN AMPUL

CROSS-REFERENCE TO RELATED APPLICATIONS

Frederick C. Mennen, application filed Oct. 29, 1971, entitled Method and Instrument for the Detection of *Neisseria Gonorrheae* Without Culture, now U.S. Pat. No. 3,876,503 granted Apr. 8, 1975.

Frederick C. Mennen, application filed Dec. 30, 1974, entitled Instrument for the Detection of Neisseria Gonorrhoeae, Ser. No. 537,593, allowed Oct. 20, 1976, Final Fee Paid Jan. 21, 1977, Now U.S. Pat. No. 4,018,653 granted Apr. 19, 1977.

Frederick C. Mennen, application filed Mar. 28, 1975, entitled Apparatus Especially Useful for Detection of *Neisseria Gonorrhoeae* and the Like in Females, Ser. No. 563,300, granted May 4, 1976, now U.S. Pat. No. 3,954,563.

Frederick C. Mennen, application filed Mar. 25, 1975, entitled Instrument for the Detection of *Neisseria Gonorrhoeae* and the Like, Ser. No. 561,707, granted May 4, 1976 now U.S. Pat. No. 3,954,564.

Frederick C. Mennen, application filed May 16, 1977, entitled Paper Booklet for Presumptive Diagnosis of *Neisseria Gonorrhoeae* in the Male, Ser. No. 797,467 granted Aug. 22, 1978, Now U.S. Pat. No. 4,108,729.

Application No. 1 is the swab series of Frederick C. Mennen entitled Over the Counter Swab Kit for Self Detection of Gonorrhea in the Male Using Saline Ampul filed on even date herewith and directed to the preferred use of the hydrochloride salt of the tetramethyl chromogen in the ampul.

BACKGROUND OF THE INVENTION a. Field of the Invention

This invention is in the field of chemistry testing, specifically analytical and analytic control employing test papers and reagent carrier wherein the device is employed in a new manner to obtain an unexpected increase in sensitivity for the direct testing of *Neisseria gonorrhea*.

The invention further lies in the field of portable testing kits such as the type of kit shown in Dutch Pat. No. 3,748,098 granted July 24, 1973 in which breakable ampuls occupy a compartment and wherein upon breakage of the ampul a solvent flows into the compartment before extraction of a testing reagent which is used in the detection of live viable bacteria.

b. Description of the Prior Art

The closest prior art on the system of testing for *Neisseria Gonorrhea* in the male is that shown in my recently issued applicaton and granted patents which are listed as follows:

Frederick C. Mennen—U.S. Pat. No. 3,876,503
Frederick C. Mennen—U.S. Pat. No. 4,018,653
Frederick C. Mennen—U.S. Pat. No. 3,954,563
Frederick C. Mennen—U.S. Pat. No. 3,954,564

Schulz U.S. Pat. No. 1,221,227 teaches iodine swab for the purpose of applying antiseptic to a cut or bruised area of the body.

Brown, et al. U.S. Pat. No. 3,835,834 shows capillary action of a swab placed in a space 20 to draw up liquid contents.

A patent to Avery, et al. U.S. Pat. No. 3,450,129, shows a system for transferring inocullum involving the use of a plastic handle fitted with a sterile swab on the end for obtaining a specimen. Swabs on a stick of this type are widely used in taking throat cultures from children and adults who suffer from respiratory infections (Q-tip type, a registered trademark).

Also known are iodine swabs holding frangible capsules.

The present invention in contrast to the Q-tip applicator sampling device conceives the utilization of a swab of the iodine swab type not for the purpose of applicator of antiseptic to an injured area but rather as a sampling means for immobilizing a specimen of living bacteria for testing gonorrhea.

Patents to Brown, et al. U.S. Pat. No. 3,835,834 and Bucalo U.S. Pat. No. 3,932,223 show the use of capillary action in containing liquid used in the culture of microorganisms or to confine liquid drawn by capillary action into a desired space. The present invention does not use the culture liquid.

SUMMARY OF THE INVENTION

The invention relates to apparatus providing an over-the-counter swab kit system for self detection of gonorrhea in the male using a tetramethyl chromogen containing frangible ampul. The kit comprises a tubular cartridge and a removable cover. The cartridge holds the chromogen in 1% solution in the ampul and a swab at the open end which projects as a tip. The tip is in the form of a swab of fibrous material which is used with the kit in the upright position with the ampul holding the chromogenic phenylenediamine salt compound and the cover removed so that a sample is taken. If gonorrhea is present it will produce a color change to deep purple after the cover is replaced and the ampul is broken to release the liquid which is colorless. A larger volume of the liquid is needed in this case to be present in the ampul in contrast with the volume of saline used in my companion case.

The preferred chemical compound which is used and incorporated into the ampul is selected from a group consisting of water soluble hydrochloride salts of phenylenediamines. The ampul holds a sufficient amount of 1% solution (about 0.5 milliliters) which will wet the tip after the ampul is broken. The ampul is a frangible ampul which is broken by simply squeezing the cartridge and serves to wet the tip through which it is drawn by capillary action after the sample of exudate has been placed, the cover replaced, the ampul broken and the color change to deep purple monitored for 3 minutes.

In the preferred embodiment the swab system for the detection andd diagnosis of living gonorrhea bacteria by chromogenic reaction uses 2 milliters of a 1% solution of substantially colorless phenylenediamine hydrochloride salt in the ampul, thereby permitting diagnosis without transport of the NG bacteria between the step of collecting the sample and testing for color change. The tubular flexible cartridge having a replaceable cover is preferably made of cellulose propionate as the thermoplastic material.

BRIEF DESCRIPTION OF THE DRAWING

FIG. 1 is a longitudinal exploded view of the diagnostic device of the present invention with the protective cover being removed therefrom;

FIG. 2 is an elevational view of the diagnostic device in position for receiving the exudate;

FIG. 3 is a longitudinal view of the device of FIG. 1 but showing the protective cover being replaced;

FIG. 4 is an elevational view showing the ampul being broken; and

FIG. 5 is a view similar to FIG. 4 but with the diagnostic device inverted to determine the results of the test.

DESCRIPTION OF THE PREFERRED EMBODIMENT

As shown in FIGS. 1 through 5 the successive steps of how to use the preferred embodiment of the diagnostic device in this case II which distinguishes over case I by using tetramethyl chromogen 26 in ampul 24 instead of saline and by employing ½ the volume, 0.5 ml of 1% solution of the chromogen than the volume of saline in the ampul of case I, which was only 1 ml of saline. Applicant has scaled these proportions down to 0.50 ml of saline and 0.25 ml of tetramethyl chromogen.

The first step illustrated in FIG. 1 is the removal of the cover 16 from the diagnostic device 8 so as to expose the projecting tip 22 of the swab which is secured at the heat seal area 20 at the open end 18 of the thermoplastic cartridge 10. The closed end 14 of the cartridge is shown in the Figs. in the form of a crimped fan shaped butt end but obviously the cartridge may be provided with an arcuate shaped bottom, as in a test tube, or with a flat bottom as in a cylinder. The advantage of the fan shaped butt portion in the present Figs. is that it permits close placement of the relatively large ampul 24 below but adjacent the bottom portion of the swab 22, thereby assuring the impregnation of the swab 22 from below with the liquid at step 4 during which step the diagnostic device 8 is squeezed to break the ampul 24 as shown by the legend in FIG. 4.

Thus, between steps 1 and 4, the following is done to the diagnostic device 8:

(1) the cover 16 is removed in FIG. 1, step 1;

(2) the sample of exudate 28 from the infected organ is applied to tip 22, as shown in FIG. 2, while the cover 16 is still removed and the device 8 is used with the cartridge 10 being substantially upright as shown in step 2 of FIG. 2;

(3) the cover 116 is then replaced over the cartridge 10 to make sure that there is no contamination to misrepresent the sample and its bacterial content as shown in step 3 and in FIG. 3;

(4) the cartridge 10 which is formed of flexible plastic is squeezed in step 4 and as shown in FIG. 4 to break the frangible ampul 24 and release its liquid contents of 1% tetramethyl chromogen with the cover replaced as in step 3 and with the cartridge *inverted,* for the first time, so that the entire liquid contents, 2 ml, flows downwardly by gravity to saturate the fibrous material of the cotton swab tip 22, at the bottom of which the exudate sample was placed in step 2, FIG. 2.

FIG. 5 shows step 5, the return of the cartridge to its normal position for the color indication of the test result, e.g., for the development of the deep purple color which is a positive test for gonorrhea.

The preferred thermoplastic material employed for the cartridge is cellulose acetate propionate which is readily available from commercial sources as listed in Volume 3, The Encyclopedia of Polymer Science and Technology, Interscience Publishers 1965, cellulose acetate butyrate may also be used but is less preferred.

The frangible ampul 24 is readily available in various sizes 0.25 ml, 0.50 ml, 0.75 ml, 1 ml, 2, ml, etc. from commercial suppliers such as the Marion Scientific Corporation, 9233 Wood Pkwy., Kansas City, Mo. 64114.

The tetramethyl chromogen is a 1% aqueous solution of N, N, N' N'-tetramethyl-p-phenylenediamine hydrochloride and the applicant has demonstrated a shelf life of at least 2 years for ampuls filled with this chromogen.

It is thus readily seen that the simplicity and built-in sanitary precautions provided by the close fitting of the relatively larger ampul 24, about 100–125% larger than the swab tip 22 provides a fool-proof yet highly effective diagnostic device for the self diagnosis of gonorrhea in the male.

Having thus disclosed the invention, what is claimed is:

1. A method for the detection and diagnosis of living gonorrhea bacteria by chromogenic reaction with a substantially colorless phenylenediamine dihydrochloride salt without transport of said bacteria from a sampling swab on which exudate from the penis of a male is placed comprising:

providing a tubular flexible cartridge having a closed end and an open end, placing a frangible ampul in said cartridge fitting a swab protruding from the open end of said cartridge above said ampul to provide a tip projecting from said cartridge, said ampul having a length at least as long as said swab and being supported by said closed end of said cartridge whereby the ampul and bottom portion of said swab substantially fill said cartridge and said ampul being filled with a substantially colorless 1% aqueous solution of N, N, N' N' tetramethyl-p-phenylenediamine dihydrochloride;

providing a cover which fits over the exposed tip of said swab to cap said cartridge;

taking a sample of exudate on the tip of the swab;

thereafter replacing said cover over said swab on said cartridge;

inverting the cartridge and cover;

breaking the ampul by squeezing the cartridge to release the aqueous solution whereby the swab is wetted by said solution and the color of the solution changes from substantially colorless to a purple color within a period of about three minutes;

waiting three minutes for the color indication of purple color and simultaneously inverting the diagnostic device in a final step;

the exudate at the tip developing this deep purple color after three minutes to show the presence of endogenous cytochrome oxidase constituting the metabolite of *Neisseria gonorrhea.*

* * * * *